US00PP21472P2

(12) United States Plant Patent
Kordes

(10) Patent No.: US PP21,472 P2
(45) Date of Patent: Nov. 16, 2010

(54) HYBRID TEA ROSE PLANT NAMED 'KORLIOLOW'

(50) Latin Name: *Rosa hybrida*
Varietal Denomination: KORliolow

(75) Inventor: Tim-Hermann Kordes, Klein Offenseth-Sparrieshoop (DE)

(73) Assignee: W. Kordes' Söhne Rosenschulen GmbH & CO KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/583,067

(22) Filed: Aug. 12, 2009

(51) Int. Cl.
*A01H 5/00* (2006.01)

(52) U.S. Cl. ..... Plt./136
(58) Field of Classification Search ..... Plt./136
See application file for complete search history.

(56) References Cited

OTHER PUBLICATIONS

2008/1238, European Union CVPO summary, Aug. 15, 2008, European Union.

*Primary Examiner*—Susan B McCormick Ewoldt

(57) ABSTRACT

A new and distinct variety of rose with long lasting, novel salmon orange-yellow flowers, and attractive foliage with good disease resistance. It exhibits uniform, upright to bushy growth with abundant flowers. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross-referenced or related applications. This variety was developed without the aid of any research grant.

SUMMARY OF THE INVENTION

Genus, species and variety denomination: The botanical classification of the new rose plant is *Rosa hybrida*, 'KORliolow'.

BACKGROUND OF THE INVENTION

The new variety of rose plant of the present invention originated from a controlled crossing made in a rose breeding program between 'KORvanaber', a non-patented rose by the same breeder, and an 'un-named seedling'.

The controlled crossing was made during the summer of 2000. The following winter, Tim-Hermann Kordes planted the resulting seeds from the aforementioned hybridization in a glasshouse where they subsequently germinated and grew. Evaluations and observations were made on the resulting seedlings in a controlled environment in Offenseth-Sparrieshoop, Germany. The resulting seedlings exhibited distinctive physical and biological characteristics. The new rose plant 'KORliolow' was selected in May, 2001 from the seedling beds to be asexually propagated for further evaluation. The first asexual reproduction of 'KORliolow' was done by budding to seedling understocks in July, 2001 at the inventor's nursery in Offenseth-Sparrieshoop, Germany.

This initial and other subsequent propagations conducted in controlled environments demonstrate that 'KORliolow' reproduces true to type in successive generations of asexual reproduction.

SUMMARY OF THE INVENTION

The new rose plant may be distinguished from its seed parent, 'KORvanaber' by the following combination of characteristics:

1. The flower color of 'KORvanaber' is cream white, while the flower color of 'KORliolow' is salmon orange-yellow.
2. The petal count of 'KORvanaber' is double, while the petal count of 'KORliolow' is very double.

The new rose plant may be distinguished from its pollen parent, an 'un-named seedling' by the following combination of characteristics:

1. The flower color of the 'un-named seedling' is orange, while the flower color of 'KORliolow' is salmon orange-yellow.
2. The petal count of the 'un-named seedling' is semi-double, while the petal count of 'KORliolow' is very double.

The objective of the hybridization was to create a new and distinct rose plant with unique qualities, such as:

1. Compact and uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORliolow' from all other varieties of which we are aware.

BRIEF DESCRIPTION OF THE DRAWING

The accompanying drawing shows as true as is reasonably possible to obtain in color photographs of this type, the typical characteristics of the buds, flowers, reproductive organs, juvenile foliage, leaves, and stems of 'KORliolow'.

DETAILED BOTANICAL DESCRIPTION

The following is a description of 'KORliolow', as observed growing in October, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORvanaber', a rose variety from the same inventor are compared to 'KORliolow' in Chart 1.

CHART 1

| Characteristic | 'KORliolow' | 'KORvanaber' |
|---|---|---|
| Average flower bloom diameter | 70-75 mm | 80-85 mm |
| Fragrance on open bloom | Light | Mild, sweet |
| Average plant height and width | 100-110 cm (h) × 65-70 cm (w) | 60 cm (h) × 50 cm (w) |

Parents:

*Seed parent.*—'KORvanaber'.

*Pollen parent.*—An 'un-named seedling'.

Classification:

*Botanical classification.*—*Rosa hybrida*, 'KORliolow'.

*Commercial classification.*—Hybrid Tea.

FLOWER AND FLOWER BUD

*Blooming habit.*—Recurrent.

*Flower bud.*—Size: Upon opening, 30 mm in length from base of receptacle to end of bud and 25 mm diameter at its widest point. Bud form: Short and ovoid to globular. Bud color: As sepals first unfold, bud color is a blend of Red Group 51B and Red-Purple Group N57A. When ¼ open, the upper surface of petals is Red Group 43C and the lower surface is a blend of Red Group 51B and Red-Purple Group N57A. Sepals: Size: Average 22-25 mm long×12-14 mm wide. Shape: Sepals generally subulate. Sepal apex is generally cirrose. Weak foliaceous appendages on three of the five sepals. Base is flat at union with receptacle. Quantity: Five. Margins: With stipitate glands on lower surface of margins. Surface texture: Inner side: Covered in fine white hairs. Outer surface: rough. Stipitate glands are absent. Color: Upper surface Yellow-Green Group 145B. Lower surface Yellow-Green Group 144B. Anthocyanin: Greyed-Purple Group 183C.

*Receptacle.*—Surface: Smooth. Color: Yellow-Green Group 144A. Shape: Urn shaped. Size: 8-9 mm (h)× 8-9 mm (w).

*Peduncle.*—Surface: With stipitate glands. Length: 35-38 mm average length. Diameter: 3.0-3.5 mm average diameter. Color: Yellow-Green Group 144B. Strength: Moderate. Borne: Multiple buds. 4-6 buds per flowering stem. Anthocyanin: Present. Greyed-Purple Group 183C.

Flower bloom:

*Fragrance.*—Light.

*Duration.*—On the plant 8-10 days. Long lasting. As a cut flower, 6 to 8 days. Senesced petals drop away cleanly.

*Size.*—Medium flowered garden rose. When open, the average flower diameter is 70-75mm and the average flower height is 30-35 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Yellow-Orange Group 19C. Inner Side: Red Group 43C. Innermost petals: Outer Side: Yellow-Orange Group 19C. Inner Side: Red Group 39B.

*Upon opening, basal petal spots.*—Basal petal spot, outermost petals: Outer Side: Yellow Group 8A. Inner Side: Yellow Group 10A. Basal petal spot, innermost petals: Outer Side: Yellow Group 8A. Inner Side: Yellow Group 10A.

*After opening, petals.*—Outermost petals: Outer Side: Yellow-Orange Group 19C. Inner Side: Red Group 43C. Innermost petals: Outer Side: Yellow Group 11C. Inner Side: Yellow Group 11C.

*After opening, basal petal spots.*—Basal petal spot, outermost petals: Outer Side: Yellow Group 8A. Inner Side: Yellow Group 10A. Basal petal spot, innermost petals: Outer Side: Yellow Group 8A. Inner Side: Yellow Group 10A. Variegations: None.

General tonality: On open flower, blend of Red Group 43C and Red Group 43D. No change in the general tonality at the end of the $4^{th}$ day. Afterwards, general tonality is a blend of Red Group 48C and Red Group 47C.

Petals:

*Petal count.*—Approximately 60-65 petals under normal conditions.

*Petal reflex.*—Petals reflex slightly.

*Petal edge.*—Ruffled with a point in center of margin.

*Petal shape.*—Quartered rosette. Apex shape is round. Shape of base is acute.

*Petal size.*—25 mm long; 24-28 mm wide.

*Thickness.*—Average.

*Petal arrangement.*—Generally in a regular pattern with overlapping edges.

Petaloids: Present.

*Petaloid count.*—Average of 10-12 per flower.

*Petaloid edge.*—Somewhat ruffled.

*Petaloid texture.*—Smooth.

*Petaloid shape.*—Linear to elliptic.

*Petaloid size.*—Petaloids are 18-20 mm long and 10-12 mm wide.

*Petaloid color.*—Color of inner side is Red Group 39B. Color of outer side is Yellow-Orange Group 19C.

Reproductive organs:

*Pistils.*—Approximately 40 present. Stigmas: Location: Slightly inferior in position to anthers. Color: Green-Yellow Group 1A. Styles: Length: 7-8 mm long. Color: Red Group 50A. Intonations of Green-Yellow Group 1C.

*Stamens.*—Approximately 65 on average and regularly arranged. Anthers: Size: 3 mm long. Color: Yellow-Orange Group 22A and Yellow-Orange Group 22B. Pollen: Absent. Filaments: Color: Yellow Group 7A. Length: 5-6 mm.

THE PLANT

*Plant growth.*—Vigorous. Upright to bushy habit. When grown as a budded nursery plant the average plant height is 100-110 cm and the average plant width is 65-70 cm.

*Stems.*—Stem color: Young wood: Yellow-Green Group 144A. Older wood: Yellow-Green Group 146C. Stem surface: Young wood: Smooth. Older wood: Rough.

*Prickles.*—Present. Incidence: 5-7 per 10 cm of stem. Size: Average length: 7-9 mm. Color: Immature prickles: Yellow-Green Group 151A. Mature prickles: Greyed-Yellow Group 160A. Senescing to Greyed-Orange Group 164C. Shape: Deeply concave. Anthocyanin: Color: Greyed-Purple Group 184A. Location: upper side of immature prickles.

*Leaves and leaflets.*—Normally 3-5 leaflets on normal leaves in middle of the stem. Leaf size: 105 mm (l)×80 mm (w). Quantity: Moderate. Texture: Upper side of leaflet: Semi-glossy. Smooth. Under side of leaflet: Matte. Rough. Leathery. Color, mature foliage: Upper Leaf Surface: Green Group 137B. Lower Leaf Surface: Yellow-Green Group 147B. Color, juvenile foliage: Upper Leaf Surface: Green Group 137B. Lower Leaf Surface: Yellow-Green Group 146B. Anthocyanin intonation: Present. Location: Intonations present on juvenile leaf margins, rachis, stipules, petiole, and stems. Color: Greyed-Purple Group 184B.

*Stipules.*—Size: 15-16 mm long. 6 mm between the tips of the stipule. Main body of stipule 6-7 mm in width. Shape: Longitudinally flanged or winged along middle. Stipule color: Yellow-Green Group 144A and Yellow-Green Group 144B. Anthocyanin: Greyed-Purple Group 184B. Presence of stipitate glands: Present on margins. Margins: Serrated. With stipitate glands.

*Petiole.*—Length: 8-12 mm. Diameter: 1.0-1.5 mm. Petiole color: Yellow-Green Group 146B. Anthocyanin present on juvenile tissue, Greyed-Purple Group 184B. Underneath: With prickles. Stipitate glands: Stipitate glands on margins.

*Petiole rachis.*—Length: 20 mm. Diameter: 1.0-1.5 mm. Color: Yellow-Green Group 146B. Margins: Stipitate glands present. Prickles: On lower sides of rachis. Stipitate glands: On margins.

*Leaflets.*—Size: Average size of the terminal leaflet is 50 mm (l)×30 mm (w). Shape: Ovate. Base: Broadly ovate. Apex: Acute. Margins: Finely serrated. Texture: Thick and leathery.

Hips/seed formation: None observed.

Winter hardiness: To date, the variety has been grown successfully in Zone 5.

Disease resistance.—Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant as herein illustrated and described:

(a) Forms attractive, long lasting salmon orange-yellow flowers;

(b) Exhibits uniform, upright and bushy growth habit;

(c) Propagates well using traditional methods, and;

(d) Exhibits very good resistance to disease under normal growing conditions, substantially as herein illustrated and described.

* * * * *

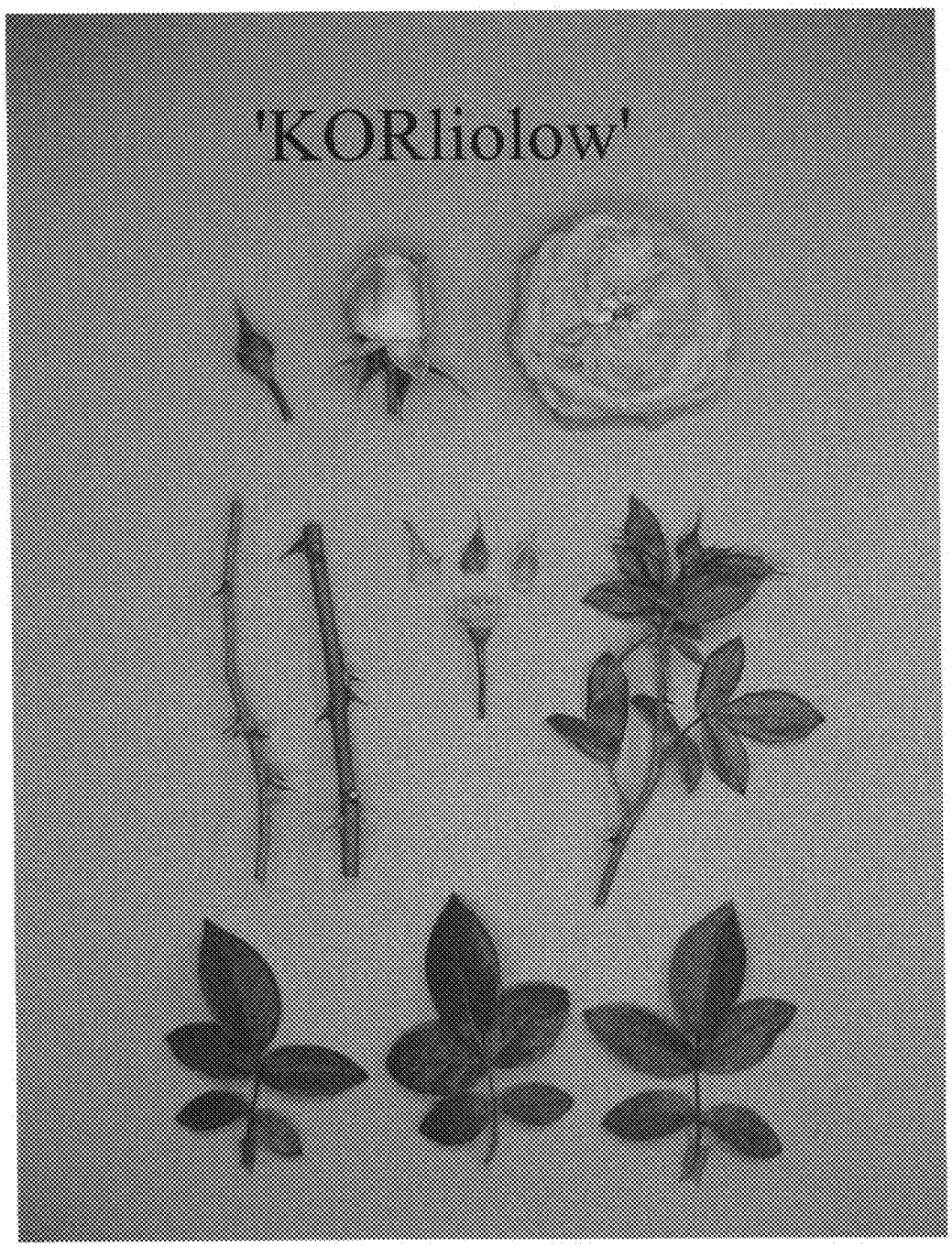
'KORliolow'